US00PP31730P2

(12) United States Plant Patent
Klemm et al.

(10) Patent No.: US PP31,730 P2
(45) Date of Patent: May 5, 2020

(54) POINSETTIA PLANT NAMED 'NPCW18087'

(50) Latin Name: *Euphorbia pulcherrima*
Varietal Denomination: NPCW18087

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/501,251

(22) Filed: Mar. 12, 2019

(51) Int. Cl.
*A01H 5/02* (2018.01)
*A01H 6/38* (2018.01)

(52) U.S. Cl.
USPC ..... Plt./307

(58) Field of Classification Search
USPC ..... Plt./307
CPC ..... A01H 5/02; A01H 5/0244; A01H 5/00; A01H 6/38; A01H 6/385
See application file for complete search history.

(56) References Cited

U.S. PATENT DOCUMENTS

PP7,825 P * 3/1992 Fruehwirth ..... Plt./307

OTHER PUBLICATIONS

Dole et al. New Poinsettias for 2018—How Did They Perform? Greenhouse Product News, retrieved on Nov. 5, 2019, retrieved from the Internet at file:///C:/Users/jhwu/Downloads/february-2018.pdf, cover page, pp. 4,16-19,22-23. (Year: 2018).*
Selecta One Poinsettia 2018, retrieved on Nov. 4, 2019, retrieved from the Internet at file:///C:/Users/jhwu/Downloads/17531_SEL_PoinsettiasCatalog2018_LR.pdf, 2 cover pages, pp. 1-2,15,25,28-29,last page (9 pp. total). (Year: 2018).*

* cited by examiner

*Primary Examiner* — June Hwu
(74) *Attorney, Agent, or Firm* — Barbara Campbell; James M. Weatherly; Cochran Freund & Young LLC

(57) ABSTRACT

A new poinsettia plant particularly distinguished by having red bracts, high vigor, and very good keeping quality is disclosed.

1 Drawing Sheet

Genus and species: *Euphorbia pulcherrima.*
Variety denomination: 'NPCW18087'.

BACKGROUND OF THE NEW PLANT

The present invention comprises a new and distinct variety of poinsettia, botanically known as *Euphorbia pulcherrima* and hereinafter referred to by the variety name 'NPCW18087'. 'NPCW18087' was derived from a cross pollination between the unpatented poinsettia 'Christmas Season' as the female parent and poinsettia 'Christmas Glory' (also known as 'NPCW12200', U.S. Plant Pat. No. 25,049) as the male parent in November 2012 in Nairobi, Kenya.

In October 2013, a single plant was selected in Stuttgart, Germany. In February and June of 2014, 'NPCW18087' was first asexually propagated by grafting onto a formerly commercial variety. The plant was pinched at six and 11 weeks post grafting, and harvested for a single plant selection 16 weeks after grafting via apical cuttings. 'NPCW18087' was found to reproduce true to type in successive generations of asexual propagation via vegetative apical cuttings in Stuttgart, Germany.

SUMMARY

The following are the most outstanding and distinguishing characteristics of this new variety when grown under normal horticultural practices in Stuttgart, Germany.

1. Red bracts and high vigor; and
2. Very good keeping quality.

DESCRIPTION OF THE PHOTOGRAPH

This new poinsettia plant is illustrated by the accompanying photograph which shows an overall view of the whole plant. The photograph is of a plant approximately 12 weeks old grown indoors in Stuttgart, Germany in December 2016. The colors shown are as true as can be reasonably obtained by conventional photographic procedures.

DESCRIPTION OF THE NEW VARIETY

The following detailed descriptions set forth the distinctive characteristics of 'NPCW18087'. The data which define these characteristics were collected from asexual reproductions carried out in Stuttgart, Germany. Data was collected on plants aged approximately 18 weeks-old after potting and grown in a glass greenhouse in Stuttgart, Germany in December 2018. Color references are to The R.H.S. Colour Chart of The Royal Horticultural Society of London (R.H.S.), $5^{th}$ edition (2007) unless where otherwise stated.

Classification:
*Family*.—Euphorbiaceae.
*Species*.—*Euphorbia pulcherrima*.
*Common name*.—Poinsettia.
*Variety*.—'NPCW18087'.

Parentage:
*Female parent*.—'Christmas Season' (unpatented).
*Male parent*.—'Christmas Glory' (U.S. Plant Pat. No. 25,049).

Growth:
*Blooming habit*.—Intermittent.
*Flowering response time*.—Approximately 50 days.
*Keeping quality*.—Very good.

Plant description:
*Form*.—Triangular.
*Growth habit*.—Upright.
*Height*.—30.0 cm to 33.0 cm.
*Width*.—27.0 cm to 31.0 cm.
*Average number of inflorescences per plant*.—5 to 6.

Propagation:
*Type cuttings*.—Apical cuttings.
*Time to produce a rooted cutting*.—4 weeks.
*Rooting habit and root color*.—Freely branching and white.

Lateral branches:
*Color*.—RHS 143A towards the upper part, gradually changing to RHS 183D.
*Length*.—27.0 cm to 28.0 cm.
*Internode length*.—1.5 cm to 4.0 cm.
*Diameter*.—0.5 cm to 0.8 cm.
*Branching habit*.—Freely branching.
*Number of lateral branches per plant*.—5 to 6.
*Texture*.—Smooth.
*Strength*.—Medium.

Leaves:
*Quantity*.—7 to 9 per lateral branch.
*Arrangement*.—Alternate.
*Number of lobes on the leaf blade*.—1 to 3.
*Lobation depth*.—Shallow.
*Depth of the deepest sinus of the leaf blade*.—0.5 cm.
*Shape*.—Ovate.
*Apex*.—Acute.
*Base*.—Obtuse.
*Margin*.—Slightly serrate, some leaves entire.
*Length*.—9.0 cm to 16.0 cm.
*Width*.—6.0 cm to 9.0 cm.
*Texture* (*both surfaces*).—Smooth.
*Vein color*.—Upper surface: Transparent. Lower surface: RHS 139D with a slightly reddish middle vein of RHS 35C.
*Venation pattern*.—Reticulate.
*Variegation*.—Absent.
*Color*.—Mature foliage: Upper surface: RHS 139A. Lower surface: RHS 139D. Immature foliage: Upper surface: RHS 141A. Lower surface: RHS 139B.
*Leaf petiole*.—Length: 3.0 cm to 6.0 cm. Diameter: 0.2 cm to 0.3 cm. Color: Upper (part) surface: RHS 59A. Lower (part) surface: RHS 181A. Texture: Smooth. Strength: Medium.
*Transitional leaves*.—Few; obtuse in shape; length is 8.0 cm to 12.0 cm; width is 5.0 cm to 8.0 cm; lobing is shallow; the green part is more towards the central part of the leaves, but where the leaves are less exposed to light, the leaves stay more green.

Inflorescence:
*Type and habit*.—Compound clusters.
*Quantity per lateral branch*.—1.
*Position relative to foliar plane*.—Above.
*Lastingness of inflorescence on the plant*.—4 weeks.
*Natural flowering season*.—Mid of November.
*Diameter*.—20.0 cm to 25.0 cm.
*Height*.—3.0 cm to 4.0 cm.
*Fragrance*.—Absent.

Bracts:
*Number of bracts per inflorescence*.—6 to 8.
*Shape*.—Ovate.
*Apex*.—Acute.
*Base*.—Obtuse.
*Margin*.—Mostly entire, older bracts slightly serrate.
*Lobing*.—Shallow.
*Rugosity between the veins*.—Medium.
*Twisting and folding along the main veins*.—Absent.
*Size*.—Length: 9.0 cm to 13.0 cm. Width: 5.0 cm to 8.0 cm.
*Texture* (*both upper and lower surfaces*).—Smooth.
*Venation pattern*.—Reticulate.
*Vein color*.—Upper surface: RHS 59A. Lower surface: RHS 181A.
*Bract color*.—Upper surface: Between RHS 46A and RHS 46B. Lower surface: Close to RHS 46B.
*Bract petiole*.—Length: 0.5 cm to 2.5 cm. Diameter: 0.2 cm to 0.3 cm. Color: Upper (part) surface: RHS 59A. Lower (part) surface: RHS 181A. Texture: Smooth. Strength: Medium.

Cyme:
*Diameter*.—1.0 cm to 2.5 cm.
*Cyathia number*.—7 to 10 per inflorescence.
*Deformation of glands of the cyathium*.—Absent.
*Timing of opening of cyathia*.—End of November. First pollen appears in parallel to opening of the nectar cups; stigmas appear 2 weeks later.
*Cyathium*.—Shape: Ovate. Texture (inner and outer surfaces): Smooth. Diameter: 0.2 cm to 0.6 cm. Length: 0.3 cm to 0.8 cm. Color: RHS 142B.
*Peduncle*.—Color: RHS 142B. Length: 0.2 cm to 0.3 cm. Diameter: 0.1 cm. Texture: Smooth. Strength: Medium.
*Nectar cups*.—Number: 1 per cyathium. Diameter: 0.1 cm. Length: 0.4 cm to 0.6 cm. Color: RHS 13B. Shape: Lip-shaped. Texture (inner and outer surfaces): Smooth.

Fruit and seed set: None observed.

Disease and pest resistance: No special disease or pest resistance observed.

COMPARISON WITH PARENTAL LINES AND KNOWN VARIETY

'NPCW18087' is a distinct variety of poinsettia. 'NPCW18087' is distinguished from its parental lines as described in Table 1.

TABLE 1

| Characteristic | 'NPCW18087' | Female Parent 'Christmas Season' | Male Parent 'Christmas Glory' |
|---|---|---|---|
| Vigor | Higher than 'Christmas Glory' | Similar to 'NPCW18087' | Lower than 'NPCW18087' |
| Earliness to flower | One week later than 'Christmas Season' | One week earlier than 'NPCW18087' | Similar to 'NPCW18087' |

'NPCW18087' is distinguished from commercial line 'Freedom Red' also known as '490' (U.S. Plant Pat. No. 7,825) as described in Table 2.

TABLE 2

| Characteristic | 'NPCW18087' | 'Freedom Red' |
|---|---|---|
| Vigor | High | Medium |
| Bract shape | More elongated and less serrate than 'Freedom Red' | Less elongated and more serrate than 'NPCW18087' |
| Cyathia quantity | Few | Many |

We claim:

1. A new and distinct variety of poinsettia plant designated 'NPCW18087' as illustrated and described herein.

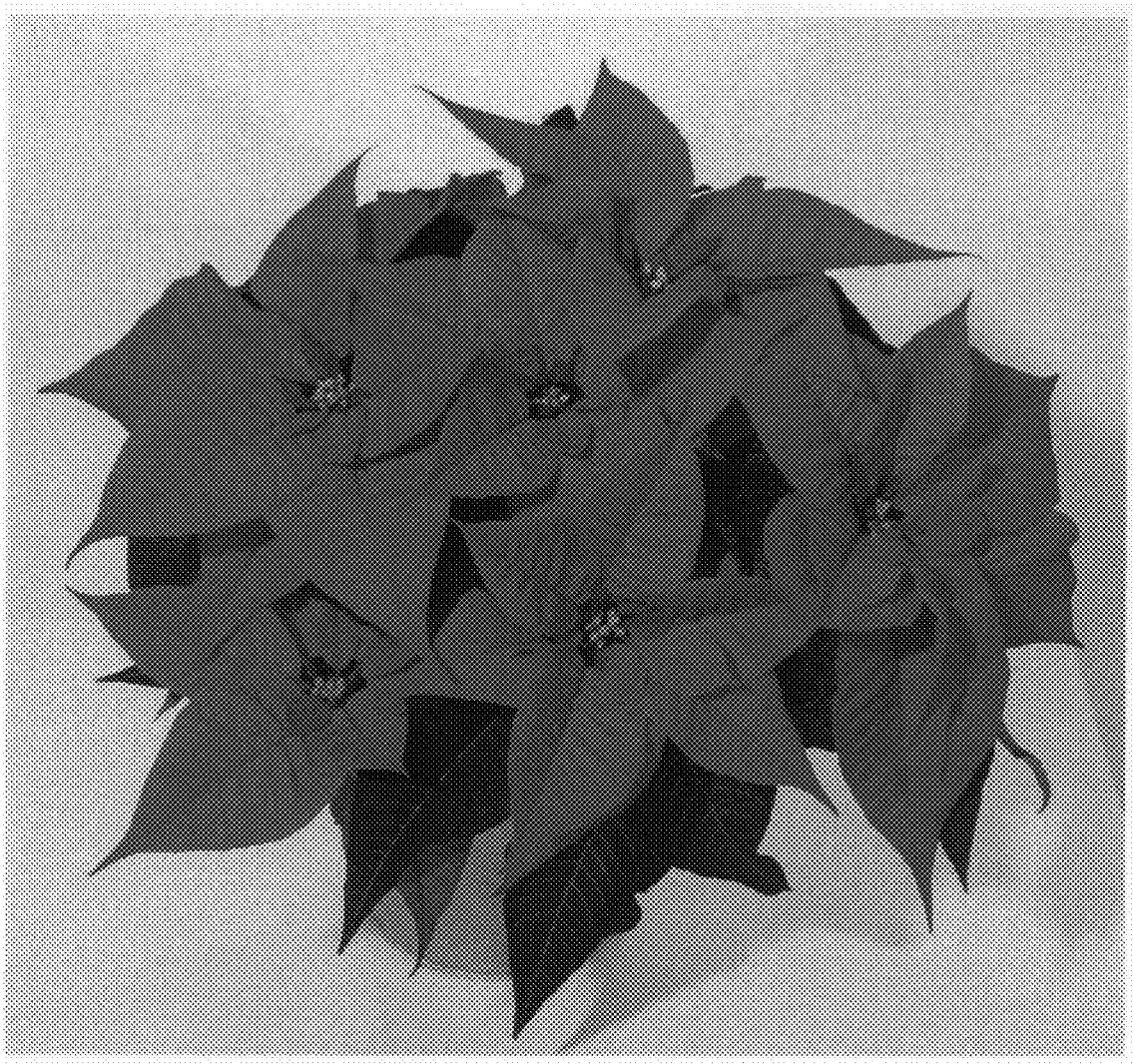

* * * * *